United States Patent
Jackson

(10) Patent No.: US 10,343,783 B2
(45) Date of Patent: Jul. 9, 2019

(54) METHOD AND APPARATUS OF DETECTING LIQUID WATER IN A CLOUD

(71) Applicant: Rosemount Aerospace Inc., Burnsville, MN (US)

(72) Inventor: Darren G. Jackson, Prior Lake, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 100 days.

(21) Appl. No.: 15/423,296

(22) Filed: Feb. 2, 2017

(65) Prior Publication Data

US 2017/0313429 A1    Nov. 2, 2017

Related U.S. Application Data

(60) Provisional application No. 62/328,984, filed on Apr. 28, 2016.

(51) Int. Cl.
*B64D 15/22* (2006.01)
*G01N 27/74* (2006.01)
(Continued)

(52) U.S. Cl.
CPC ............ *B64D 15/22* (2013.01); *B64D 15/12* (2013.01); *B64D 15/20* (2013.01); *B64D 43/02* (2013.01);
(Continued)

(58) Field of Classification Search
None
See application file for complete search history.

(56) References Cited

U.S. PATENT DOCUMENTS 3,341,835 A * 9/1967 Werner ................. B64D 15/20
340/582
3,508,435 A * 4/1970 Ivy ....................... G01N 27/223
73/61.43
(Continued)

FOREIGN PATENT DOCUMENTS

| CN | 2692643 A2 | 2/2014 | |
| DE | 001572994 A1 * | 5/1969 | ............. B06B 1/085 |
| WO | 0216201 A1 | 2/2002 | |

OTHER PUBLICATIONS

Henderson, Thomas J., and Mark E. Solak. "Supercooled Liquid Water Concentrations in Winter Orographic Clouds from Ground-base Ice Accretion Measurements." The Journal of Weather Modification 15.1 (2012): 64-70.*

(Continued)

*Primary Examiner* — Daniel S Larkin
(74) *Attorney, Agent, or Firm* — Kinney & Lange, P.A.

(57) ABSTRACT

Apparatus and associated methods relate to determining liquid-water concentration in a cloud atmosphere based on a frequency of resonance of a magnetostrictive resonator and/or a temporal variation of the resonant frequency of the magnetostrictive resonator. The magnetostrictive resonator is configured to resonate at a resonant frequency indicative of a measure of ice accumulation upon an exterior surface of the magnetostrictive resonator. When in liquid-water ambient, however, the magnetostrictive resonator has a resonant frequency less than a baseline resonant frequency. When in the liquid-water ambient, the magnetostrictive resonator also has temporal variations in resonant frequency that exceed one part in ten thousand. Using one or both of these resonant-frequency responses to liquid-water ambient, a signal indicative of liquid-water content can be generated.

20 Claims, 6 Drawing Sheets

(51) Int. Cl.
*B64D 43/02* (2006.01)
*G01N 33/00* (2006.01)
*B64D 15/12* (2006.01)
*B64D 15/20* (2006.01)
*G01N 29/036* (2006.01)
*G01N 29/24* (2006.01)
*G01N 29/32* (2006.01)
*G01N 29/44* (2006.01)

(52) U.S. Cl.
CPC ........... *G01N 27/74* (2013.01); *G01N 29/036* (2013.01); *G01N 29/2412* (2013.01); *G01N 29/326* (2013.01); *G01N 29/4436* (2013.01); *G01N 33/0036* (2013.01); *G01N 2291/0251* (2013.01); *G01N 2291/02845* (2013.01); *G01N 2291/2694* (2013.01)

(56) References Cited

U.S. PATENT DOCUMENTS

| | | | |
|---|---|---|---|
| 4,404,852 A | | 9/1983 | Goto |
| 6,320,511 B1 | | 11/2001 | Cronin et al. |
| 9,242,735 B1 | | 1/2016 | Meis et al. |
| 2005/0030332 A1* | 2/2005 | Masuda | ................. B41J 29/393 347/19 |
| 2005/0116831 A1* | 6/2005 | Zribi | .................... G01N 29/036 340/632 |
| 2005/0230553 A1* | 10/2005 | Otto | ....................... B64D 15/20 244/134 F |
| 2005/0262943 A1* | 12/2005 | Claydon | ............... G01N 29/022 73/579 |
| 2006/0050765 A1* | 3/2006 | Walker | ..................... G01K 7/32 374/109 |
| 2012/0135324 A1* | 5/2012 | Nishikawa | ........ H01M 8/04171 429/414 |
| 2014/0037446 A1* | 2/2014 | Garnett | .................. B64D 15/14 416/1 |
| 2017/0030848 A1* | 2/2017 | Borigo | ................... B64D 15/20 |

OTHER PUBLICATIONS

Jackson, Darren, et al. "Ludlam limit considerations on cylinder ice accretion—Aerodynamics and thermodynamics." 39th Aerospace Sciences Meeting and Exhibit. 2001.*

Cober, Stewart G., George A. Isaac, and Alexei V. Korolev. "Assessing the Rosemount icing detector with in situ measurements." Journal of Atmospheric and Oceanic Technology 18.4 (2001): 515-528.*

Brown, Emery N. An evaluation of the Rosemount ice detector for aircraft hazard warning and for undercooled cloud water content measurements. No. 183. High Altitude Observatory, National Center for Atmospheric Research, 1981.*

Extended European Search Report, for European Patent Application No. 17168306.3, dated Oct. 12, 2017, 9 pages.

* cited by examiner

METHOD AND APPARATUS OF DETECTING LIQUID WATER IN A CLOUD

CROSS-REFERENCE TO RELATED APPLICATION(S)

This application claims the benefit of U.S. Provisional Application No. 62/328,984 filed Apr. 28, 2016 for "METHOD AND APPARATUS OF DETECTING LIQUID WATER IN A CLOUD" by Darren G. Jackson.

BACKGROUND

Clouds can present risks to aircraft when traveling through them. When in a cloud, ice can form on control surfaces and/or lift surfaces. When aircraft engines ingest excessive moisture, the chemistry of combustion can change. Large ice particles can be abrasive to exposed surfaces of aircraft engines. And very large ice particles can even damage aircraft engines. Not every cloud, however, presents these hazards to an aircraft. Different clouds and different atmospheric conditions may be accompanied by various water droplet size distributions, different ice/liquid ratios, etc., some of which may be entirely safe to an aircraft. Such water droplet size distributions and ice/liquid ratios may be measured as cloud metrics using various instruments.

Some aircraft are equipped with these instruments to detect ice accretion on an exterior surface of the aircraft. Magnetostrictive resonators have been used for such purposes. A resonant frequency of the magnetostrictive resonator changes in response to ice accumulation on a resonator. The ice accumulation changes the mass of the resonator, which in turn changes the frequency of resonance. Liquid water, in contrast to accreted ice, does not fixedly attached to an exterior surface of an aircraft. Direct methods of detecting liquid water on an aircraft surface have been more difficult to perform.

SUMMARY

Apparatus and associated devices relate to a cloud phase detector that includes a magnetostrictive resonator having a baseline resonant frequency in an ice-free and liquid-water-free condition. The magnetostrictive resonator is configured to resonate at a resonant frequency indicative of a measure of ice accretion upon an exterior surface of the magnetostrictive resonator. The cloud phase detector includes a liquid-water detection system configured to generate a signal indicative of liquid-water content of a cloud. The liquid-water detection system includes a frequency detector configured to detect the resonant frequency of the magnetostrictive resonator. The liquid-water detection system includes a noise detector configured to detect temporal variations of the resonant frequency of the magnetostrictive resonator. The liquid-water detection system is configured to generate a signal indicative of the liquid-water content if either the detected resonant frequency is a first threshold less than the baseline resonant frequency or the detected temporal variations of the resonant frequency are greater than a second threshold.

In some embodiments, a liquid-water content calculator includes a magnetostrictive resonator having a baseline resonant frequency in an ice-free and liquid-water-free condition. The magnetostrictive resonator is configured to resonate at a resonant frequency indicative of a measure of ice accretion on an exterior surface of the magnetostrictive resonator. The liquid-water content calculator includes a frequency detector configured to detect the resonant frequency of the magnetostrictive resonator. The liquid-water content calculator includes a noise detector configured to detect temporal variations of the resonant frequency of the magnetostrictive resonator. The liquid-water content calculator includes a liquid-water detection system configured to generate a signal indicative of the liquid-water content if either the detected resonant frequency is a first threshold less than the baseline resonant frequency or the detected temporal variations of the resonant frequency are greater than a second threshold. The liquid-water content calculator includes an ambient temperature detector configured to generate a signal indicative of an ambient temperature. The liquid-water content calculator includes an airspeed indicator configured to detect airspeed of an aircraft. The liquid-water content calculator includes an angle-of-attack sensor configured to detect an angle of attack of the aircraft. The liquid-water content calculator also includes a critical temperature calculator configured to calculate, based on the detected airspeed, the detected angle of attack, the detected ambient temperature, the detected resonant frequency, and the detected temporal variations of the resonant frequency, one or more critical temperatures corresponding to one or more locations on an aircraft surface, respectively. The one or more critical temperatures are indicative of a temperature below which a freezing fraction of the liquid-water content is greater than zero.

In some embodiments, a method for determining liquid-water content in a cloud includes presenting a resonator in a cloud. The method includes magnetostrictively resonating the resonator. The method includes determining a baseline resonant frequency of the resonator. The method includes measuring a frequency of resonance of the resonator in the cloud. The method includes comparing the measured frequency of resonance with the determined baseline resonant frequency. The method includes determining a temporal variation of the measured frequency of resonance. The method includes comparing the determined temporal variation of the measured frequency of resonance with a predetermined threshold. The method includes generating a signal indicative of liquid-water content. The generated signal indicative of liquid-water content is zero if the compared frequency of resonance is not less than the determined baseline resonant frequency and the compared temporal variation is not greater than the predetermined threshold. The generated signal indicative liquid-water content is greater than zero if either the compared frequency of resonance is a first threshold less than the determined baseline resonant frequency or the compared temporal variation is greater than a second threshold.

DETAILED DESCRIPTION

Apparatus and associated methods relate to generating a measure of liquid-water content of a cloud using either ice accretion detection or liquid-water detection or both using a magnetostrictive resonator. Magnetostrictive resonators have been used to measure ice accretion on an exterior surface of aircraft, but heretofore have not been used for determining liquid-water presence on such exterior surfaces. Exposure of a magnetostrictive resonator to an atmosphere that has liquid-water droplets can cause these magnetostrictive resonators to resonate at a frequency lower than a baseline resonant frequency. Furthermore, when exposed to an atmosphere that has liquid-water droplets, the measured resonant frequency has a temporal variation that is greater than a baseline temporal variation. By using one or both of these indicia, a measure of liquid-water content of a cloud can be generated using a magnetostrictive resonator.

Figure 1:
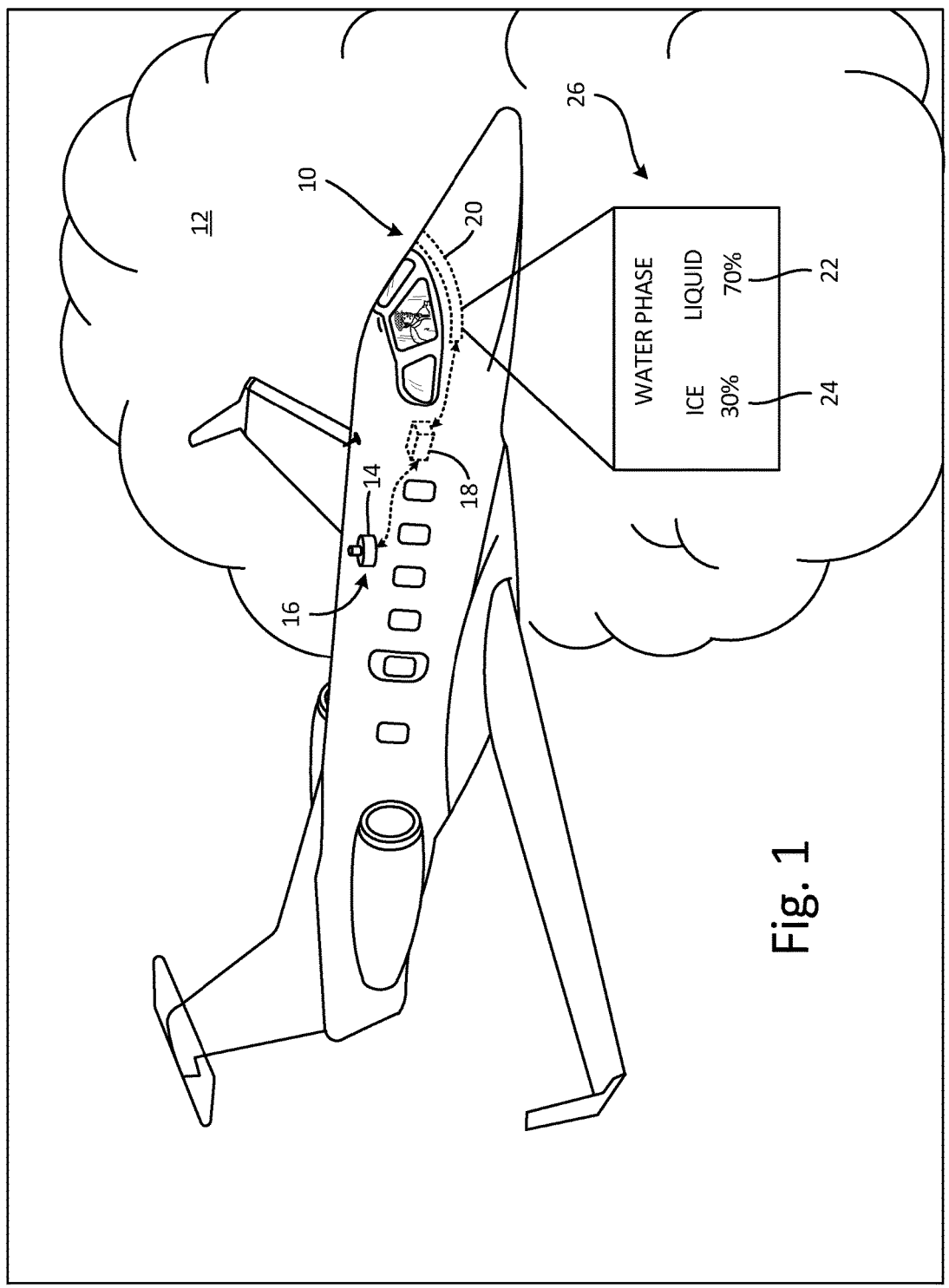
FIG. 1 is a perspective view of an aircraft having water accretion detector configured to perform both ice accretion detection and liquid water detection.

FIG. 1 is a perspective view of an aircraft having ice accretion detector configured to perform both ice accretion detection and liquid-water detection. In FIG. 1, aircraft 10 is flying through cloud 12. Aircraft 10 has magnetostrictive resonator 14 affixed to exterior surface region 16. Magnetostrictive resonator 14 generates a signal indicative of a resonant frequency and provides such a signal to phase determination system 18. Phase determination system 18 is in electrical communication with avionics system 20, and provides water phase information 22, 24 for display on cockpit display device 26. In this exemplary embodiment, cockpit display device 26 indicates liquid-water presence 22 and ice accretion 24. The depicted accretion detector can advantageously provide pilot 28 with both ice accretion data 24 and liquid-water data 22.

In some embodiments, magnetostrictive resonator 14 will have a baseline resonant frequency when exposed to an ice-free and liquid-water-free atmosphere. As ice is accreted upon magnetostrictive resonator 14, the resonant frequency of magnetostrictive resonator will decrease. The resonant frequency will continue decreasing as ice continues to accrete on the magnetostrictive resonator 14. When the resonant frequency of the magnetostrictive resonator 14 falls below a predetermined limit due to accretion of ice, a built-in heating element heats up magnetostrictive resonator 14 until the accreted ice has been completely melted and/or sublimated. Magnetostrictive resonator 14 then will again be monitored.

Thus, ice accretion causes a decreasing resonant frequency of magnetostrictive resonator 14. Atmospheres having liquid-water droplets also can affect the resonant frequency of magnetostrictive resonators. For example, a droplet that impinges upon magnetostrictive resonator 14 can add its mass to a mass of the magnetostrictive resonator 14. Although the liquid-water droplets may only partially adhere to magnetostrictive resonator 14, the mass of even a partial droplet can contribute to the mass of magnetostrictive resonator 14. Magnetostrictive resonator 14, when resonating, involves an axial oscillatory movement of magnetostrictive resonator 14. This axial oscillatory movement can be affected by any water droplets contributing to the moving mass of magnetostrictive resonator 14. Thus, impinging liquid-water droplets affect the resonant frequency of magnetostrictive resonator 14, but to a lower degree than ice accretion.

The resonant frequency of magnetostrictive resonator 14 is affected in at least two ways by impinging liquid water droplets. First, the resonant frequency decreases with any additional mass associated with liquid water droplets. And second, the resonant frequency has temporal variations in response to temporal variations of liquid water droplet attachment to magnetostrictive resonator 14. These two indicia: i) a decrease in resonant frequency; and ii) an increase in temporal variation of resonant frequency, can either individually or together be used to determine liquid-water content in a cloud atmosphere.

Figure 2B:
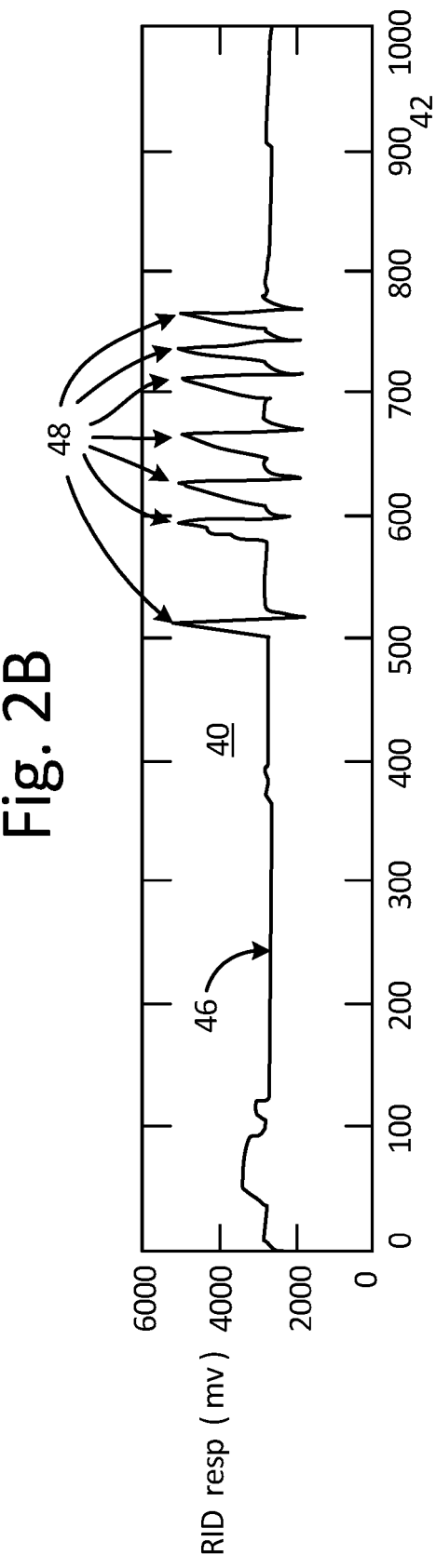
FIGS. 2A-2B are a graph of liquid-water content and a graph of an ice detection signal from a magnetostrictive resonator during a flight through a cloud.
Figure 2A:
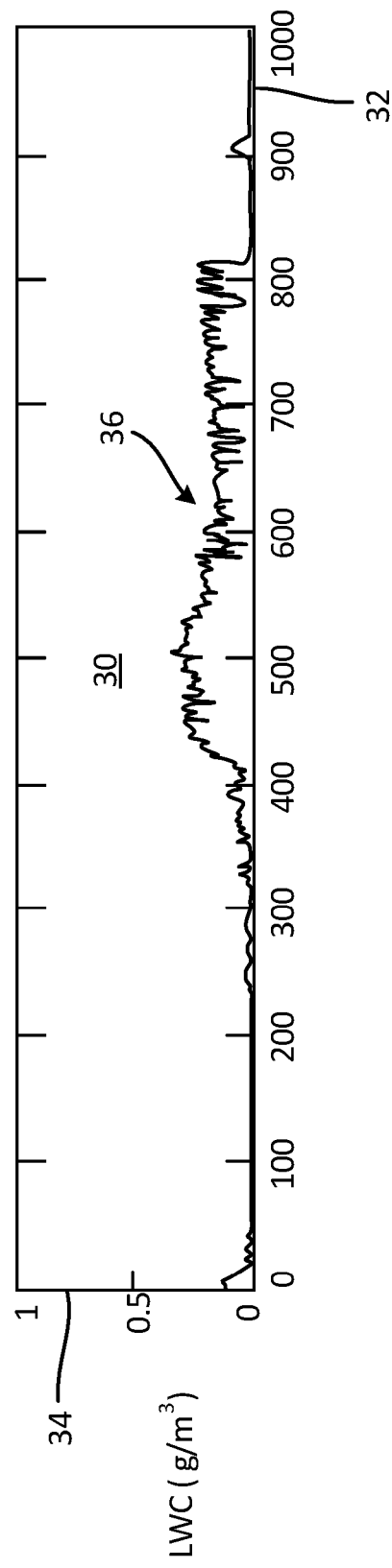

FIG. 2A is a graph of liquid-water content and FIG. 2B is a graph of an output signal from a magnetostrictive resonator during a flight through a cloud. In FIG. 2A, graph 30 has horizontal axis 32, which represents a time of flight. Graph 30 also has vertical axis 34, which indicates liquid-water content (LWC) of the atmosphere. The liquid-water content is indicated in units of $g/mm^2$. Graph 30 shows LWC/time relation 36. LWC/time relation 36 begins at time equal to zero and continues until time equal to 1000. At time equal to about 350, LWC/time relation 36 indicates that the aircraft is entering a cloud atmosphere that has non-zero liquid-water content. The aircraft remains in a non-zero liquid-water content atmosphere until time equals about 815. Additionally, the aircraft encounters a non-zero liquid-water content atmosphere briefly at two other times during the flight: i) at time equal about zero; and ii) at time equal about 900.

In FIG. 2B, graph 40 corresponds to the same flight that recorded LWC/time relation 36 depicted in graph 30. Graph 40 has horizontal axis 42, which also represents a time of flight. Graph 40 has vertical axis 44, which indicates an output signal of magnetostrictive resonator 14. The output signal is inversely related to a resonant frequency of magnetostrictive resonator 14. The output signal is indicated in units of mV. Graph 40 shows output-signal/time relation 46. Output-signal/time relation 46 includes seven triangle-like signal portions 48. Each of triangle-like signal portions 48 is indicative of ice accretion. For example, at time equal about 500, output-signal/time relation begins to increase from a baseline value of about 3000 mV. Output-signal/time relation monotonically increases until time equals about 515 at which point output signal equals about 5000 mV. An internal heater is activated at time equal to about 515, which melts and or sublimates any ice accreted onto magnetostrictive resonator 14. Magnetostrictive sensor 14 is given time to cool and measurements proceed again. No additional ice accretion occurs until time equals about 580. Then ice accretion continues virtually unabated until time equals about 775.

Magnetostrictive resonator 14 is thus capable of measuring ice accretion on an exterior surface of the aircraft. Magnetostrictive resonator 14 can also indicate when liquid-water droplets impinge upon magnetostrictive resonator 14. As shown in FIG. 2B, at the three times 0, 350 and 900 in which the aircraft enters a non-zero liquid-water content atmosphere, output-signal/time relation 46 shows a modest increase. Similarly, notice that when the aircraft emerges from the non-zero liquid-water content atmospheres, at time equal to about 20, 8215 and 915, output-signal/time relation 46 shows a modest decrease. Furthermore, whenever the aircraft is in a non-zero liquid water atmosphere, the resonant frequency has greater temporal variation than when the aircraft is in a zero liquid water atmosphere.

Figure 3:
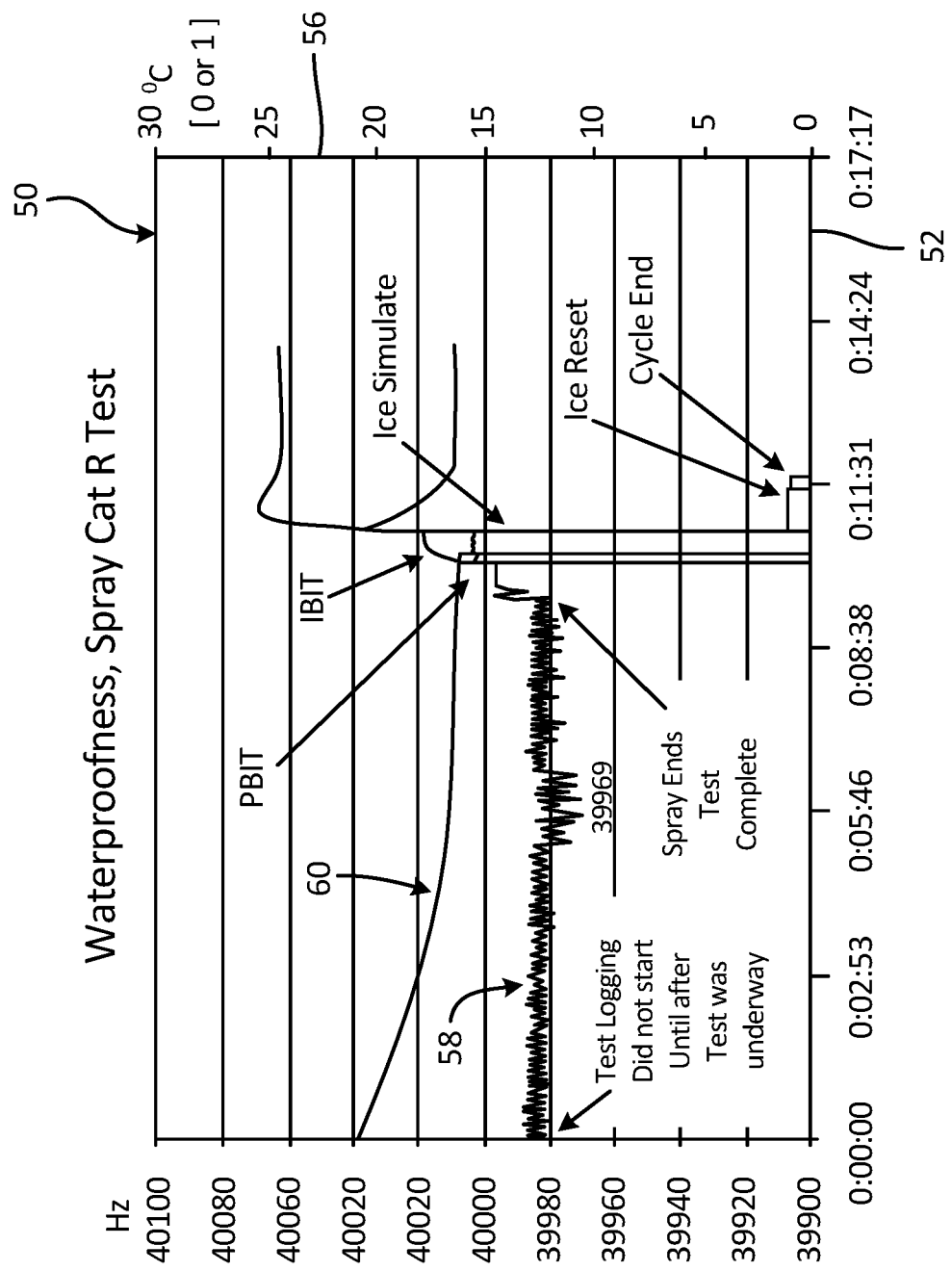
FIG. 3 is a graph of a resonant frequency of a magnetostrictive resonator during exposure to an atmosphere having liquid-water content.

FIG. 3 is a graph of a resonant frequency of a magnetostrictive resonator during exposure to an atmosphere having liquid-water content. In FIG. 3, graph 50 has horizontal axis 52 and two vertical axes 54, 56. Horizontal axis 52 is indicative of time. First vertical axis 54 is indicative of frequency of resonance of magnetostrictive resonator 14, and has units of Hz. Second vertical axis 56 is indicative of ambient temperature (e.g., atmospheric temperature), and has units of ° C. Graph 50 has two relations 58, 60 plotted thereon. Relation 58 is indicative of the frequency of resonance of magnetostrictive resonator 14. Relation 60 is indicative of the temperature of the atmosphere in which magnetostrictive resonator 14 is located.

At time equal to zero, the test logging began with the test already underway. From time equal to about zero through time equal to about 9:00, a non-zero liquid atmosphere is simulated using sprayed water. The resonant frequency throughout this portion of the testing is about 39,983 Hz. The temporal variation of the resonant frequency during this portion of the testing is about plus or minus 4 Hz. During a second portion of the testing, between the time of about 9:00 and about 10:00, no water is sprayed onto magnetostrictive resonator 14. During this portion of the testing, the resonant frequency of magnetostrictive resonator 14 is about 39,998 Hz. And during this portion of the testing the temporal variation of the resonant frequency is near zero.

In some embodiments, the magnitude of the temporal variations of the resonant frequency may be indicative of a mean liquid water droplet size. In some embodiments, an ice/liquid water ratio may be determined using both the resonant frequency and the temporal variation of resonant frequency of the magnetostrictive resonator.

Figure 4:
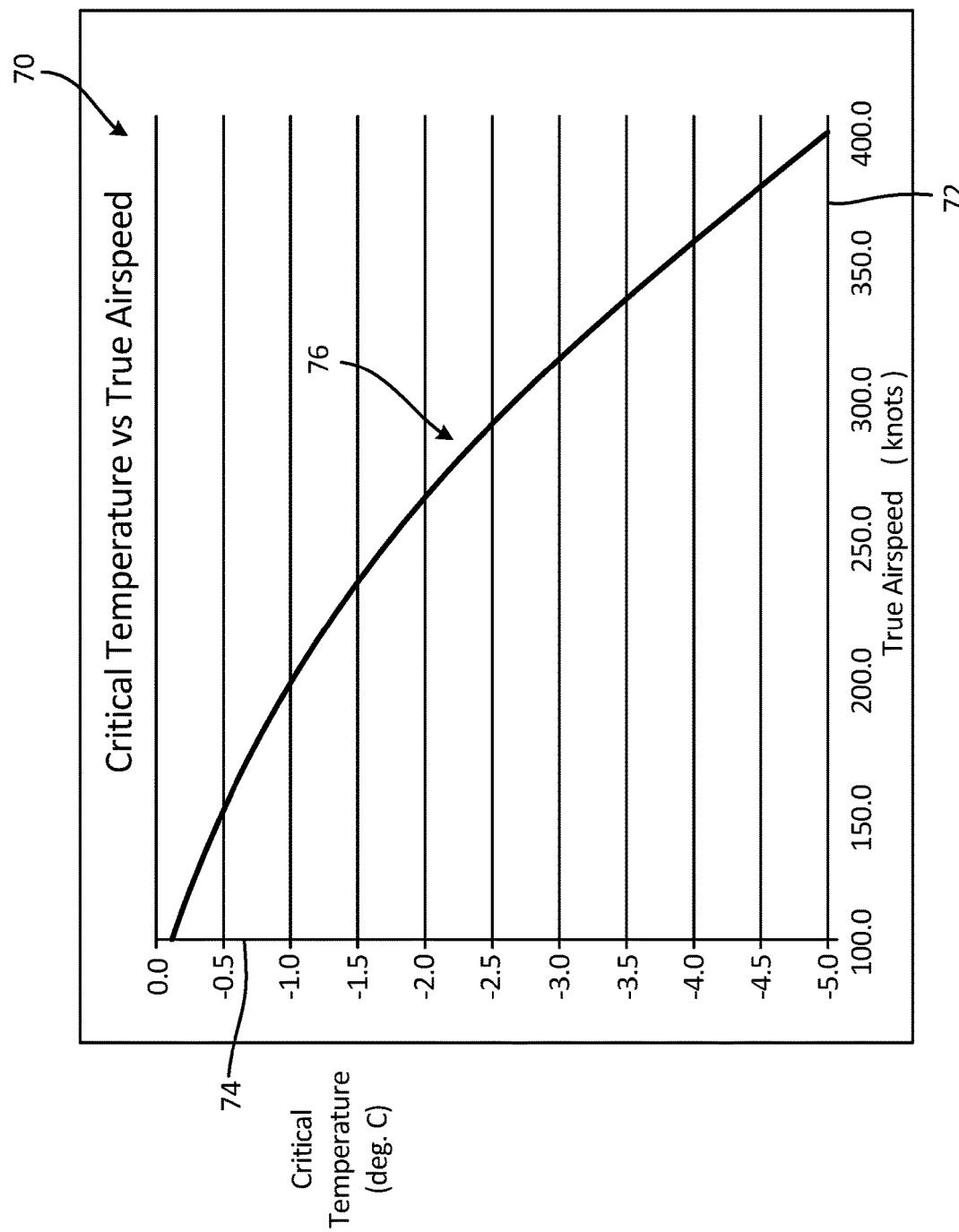
FIG. 4 is a graph of a critical temperature vs. airspeed for a given angle of attack.

FIG. 4 is a graph of a critical temperature vs. airspeed for a given angle of attack. In FIG. 4, graph 70 includes horizontal axis 72 and vertical axis 74. Horizontal axis 72 is indicative of airspeed of an aircraft. Vertical axis 74 is indicative of a critical temperature. Critical temperature is a temperature below which supercooled liquid-water droplets can begin to freeze on an exterior surface. Graph 70 shows critical temperature/airspeed relation 76. Critical temperature/airspeed relation 76 indicates that critical temperature decreases with increasing airspeed. Other aerodynamic factors can similarly affect critical temperature. For example, angle of attack can affect critical temperature. Such graphs, as exemplified by graph 70 of FIG. 4, can be used to predict critical temperatures of various surface locations on an airplane.

Figure 5:
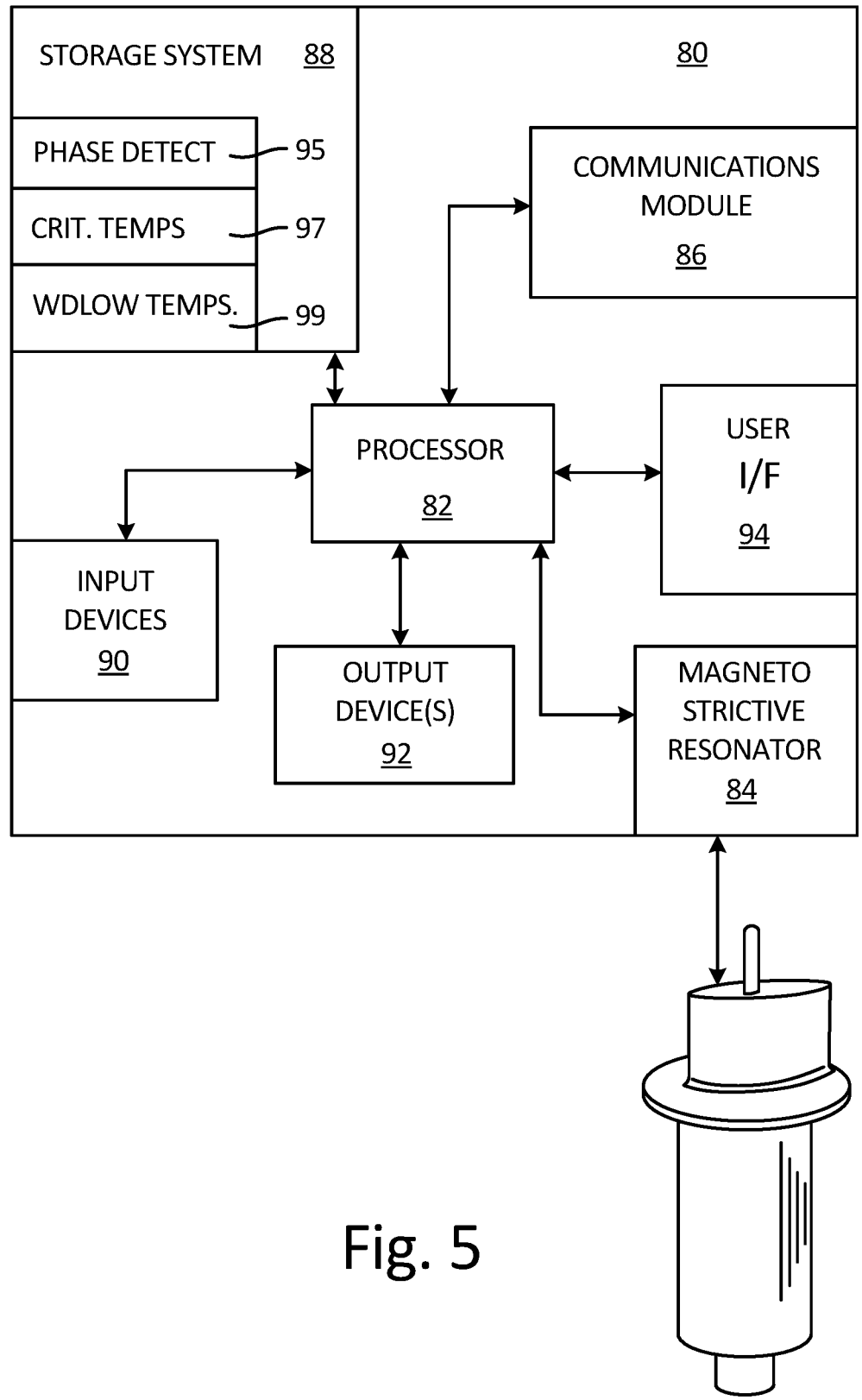
FIG. 5 is a block diagram of an exemplary cloud phase detection system.

FIG. 5 is a block diagram of an exemplary cloud phase detection system. In the depicted configuration, cloud phase detection system 18 includes magnetostrictive resonator 14 coupled to device 80 that can implement cloud phase detection. Device 80 can be any device capable of executing computer-readable instructions defining a software program implementing long-range cloud conditions detection. Examples of device 80 can include, but are not limited to, laptop computers, mobile phones (including smartphones), tablet computers, personal digital assistants (PDAs), desktop computers, servers, mainframes, or other computing devices. In some examples, device 80 can be an avionics unit configured for use on an aerial vehicle, such as a helicopter, unmanned aerial vehicle (UAV), or other aircraft.

As illustrated in FIG. 5, device 80 includes processor 82, magnetostrictive resonator interface 84, communications module 86, storage system 88, input devices 90, output devices 92, and user interface 94. However, in certain examples, device 80 can include more or fewer components. For instance, in examples where device 80 is an avionics unit, device 80 may not include input device(s) 90 and/or output device(s) 92. In some examples, such as where device 80 is a mobile or portable device such as a laptop computer, device 80 may include additional components such as a battery that provides power to components of device 80 during operation.

Processor(s) 82, in one example, are configured to implement functionality and/or process instructions for execution within device 80. For instance, processor(s) 82 can be capable of processing instructions stored in storage device(s) 88. Examples of processor(s) 82 can include any one or more of a microprocessor, a controller, a digital signal processor (DSP), an application specific integrated circuit (ASIC), a field-programmable gate array (FPGA), or other equivalent discrete or integrated logic circuitry.

Storage device(s) 88 can be configured to store information within device 80 during operation. Storage device(s) 88, in some examples, are described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, storage device(s) 88 are a temporary memory, meaning that a primary purpose of storage device(s) 88 is not long-term storage. Storage device(s) 88, in some examples, are described as volatile memory, meaning that storage device(s) 88 do not maintain stored contents when power to device 80 is turned off. Examples of volatile memories can include random access memories (RAM), dynamic random access memories (DRAM), static random access memories (SRAM), and other forms of volatile memories. In some examples, storage device(s) 88 are used to store program instructions for execution by processor(s) 82. Storage device(s) 88, in one example, are used by software or applications running on device 80 (e.g., a software program implementing cloud phase detection) to temporarily store information during program execution.

Storage device(s) 88, in some examples, also include one or more computer-readable storage media. Storage device(s) 88 can be configured to store larger amounts of information than volatile memory. Storage device(s) 88 can further be configured for long-term storage of information. In some examples, storage device(s) 88 include non-volatile storage elements. Examples of such non-volatile storage elements can include magnetic hard discs, optical discs, floppy discs, flash memories, or forms of electrically programmable memories (EPROM) or electrically erasable and programmable (EEPROM) memories. Storage device(s) 88 can include liquid-water detection segments 95, critical temperature calculator segment 97, and Ludlam temperature calculator segment 99.

Device 80, in some examples, also includes communications device(s) 86. Device 80, in one example, utilizes communication device(s) 86 to communicate with external devices via one or more networks, such as one or more wireless or wired networks or both. Communications device(s) 86 can be a network interface card, such as an Ethernet card, an optical transceiver, a radio frequency transceiver, or any other type of device that can send and receive information. Other examples of such network interfaces can include Bluetooth, 3G, 4G, and WiFi radio computing devices as well as Universal Serial Bus (USB).

Device 80, in some examples, also includes input device(s) 90. Input device(s) 90, in some examples, are configured to receive input from a user. Examples of input device(s) 90 can include a mouse, a keyboard, a microphone, a camera device, a presence-sensitive and/or touch-sensitive display, or other type of device configured to receive input from a user.

Output device(s) 92 can be configured to provide output to a user. Examples of output device(s) 92 can include a display device, a sound card, a video graphics card, a speaker, a cathode ray tube (CRT) monitor, a liquid crystal display (LCD), a light emitting diode (LED) display, an organic light emitting diode (OLED) display, or other type of device for outputting information in a form understandable to users or machines.

Accordingly, device 80 illustrates one example embodiment of a device that can execute a software program including a plurality of segments that each includes one or more modules implementing an interface that enables direct communication between the respective module and modules that are members of any other of the plurality of segments.

Figure 6:
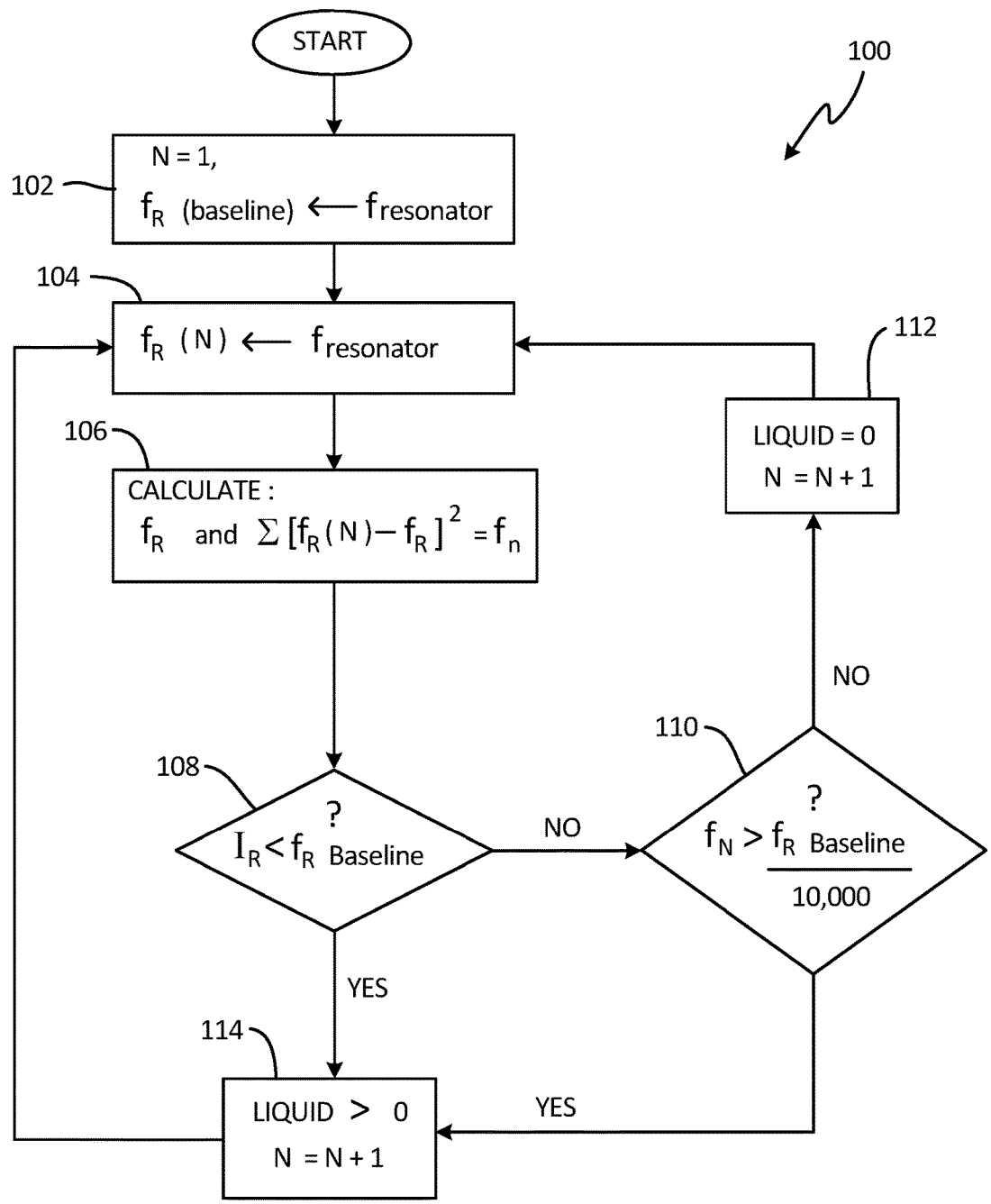
FIG. 6 is a flow chart of an exemplary method of detecting cloud conditions from a distance.

FIG. 6 is a flow chart of an exemplary method of detecting cloud conditions from a distance. In FIG. 6, method 100 is depicted from the vantage point of processor 82 of FIG. 5. Method 100 begins at step 102 with processor 82 initializing index N to one, and establishing a baseline resonant frequency $f_R(\text{BASELINE})$. Then, at step 104, processor 82 receives a measurement of the resonant frequency $f_R(N)$ of magnetostrictive resonator 14. At step 106, processor 82 calculates both a running mean resonant frequency $\bar{f}_R$ and a measure of noise $f_N^2 = \Sigma_N (f_R(N) - \bar{f}_R)^2$. The running mean can be taken for the last M samples, for example, and the noise can be calculated over these same M samples. Then at step 108, processor 82 compares the mean resonant frequency $\bar{f}_R$ with the baseline resonant frequency $f_R(\text{BASELINE})$. If the mean resonant frequency $\bar{f}_R$ is not less than the baseline resonant frequency $f_R(\text{BASELINE})$, then method 100 proceeds to step 110 where processor 82 compares the calculated noise $f_N$ with a fraction (e.g., one ten-thousandth) of the baseline resonant frequency $f_R(\text{BASELINE})$. If, at step 110, the calculated noise $f_N$ is not greater than the fraction of the baseline resonant frequency $f_R(\text{BASELINE})$, then processor 82 increases index N and determines a liquid-water content of the cloud is zero. Method 100 then returns to step 104. If, however, either at step 108 or at step 110, the comparison was evaluated in the affirmative, then method 100 proceeds to step 114 where processor 82 increases index N and determines the liquid-water content is greater than zero. Then, method 100 again returns to step 104.

In various embodiments, various thresholds are used in the comparisons performed at steps 108 and 110. For example, in some embodiments, at step 108 processor 82 compares mean resonant frequency $\bar{f}_R$ with a product of baseline resonant frequency $f_R(\text{BASELINE})$ and a factor less than 1. For example processor 82 may determine whether mean resonant frequency $\bar{f}_R$ is at least one-ten thousandths of the baseline resonant frequency $f_R(\text{BASELINE})$ less than the baseline resonant frequency $f_R(\text{BASELINE})$. In an exemplary embodiment, processor 82 may determine whether mean resonant frequency $\bar{f}_R$ is at least three-ten thousandths of the baseline resonant frequency $f_R(\text{BASELINE})$ less than the baseline resonant frequency $f_R(\text{BASELINE})$ (e.g., less than 0.9997 times $f_R(\text{BASELINE})$). In some embodiments, processor 82 may compare calculated noise $f_N$ with various fractions of the baseline resonant frequency $f_R(\text{BASELINE})$. For example, processor may compare $f_N$ with about one, two, three or about five ten-thousandths of the baseline resonant frequency $f_R(\text{BASELINE})$.

The following are non-exclusive descriptions of possible embodiments of the present invention.

A cloud phase detector includes a magnetostrictive resonator having a baseline resonant frequency in an ice-free and liquid-water-free condition. The magnetostrictive resonator is configured to resonate at a resonant frequency indicative of a measure of ice accretion upon an exterior surface of the magnetostrictive resonator. The cloud phase detector includes a liquid-water detection system configured to generate a signal indicative of liquid-water content of a cloud. The liquid-water detection system includes a frequency detector configured to detect the resonant frequency of the magnetostrictive resonator. The liquid-water detection system includes a noise detector configured to detect temporal variations of the resonant frequency of the magnetostrictive resonator. The liquid-water detection system is configured to generate a signal indicative of the liquid-water content if either the detected resonant frequency is a first threshold less than the baseline resonant frequency or the detected temporal variations of the resonant frequency are greater than a second threshold.

The cloud phase detector of the preceding paragraph can optionally include, additionally and/or alternatively, any one or more of the following features, configurations and/or additional components: a temperature sensor; a digital communications interface; and an ice-phase detection system. The temperature sensor can be configured to generate a signal indicative of the temperature of an exterior surface of the cloud phase detector. The digital communications interface can be configured to receive digital communications from an aircraft instrumentation bus. The received digital communications can include a signal indicative of airspeed of an aircraft and a signal indicative of an angle of attack of the aircraft. The ice-phase detection system can be configured to generate a signal indicative of a rate of the ice accretion. The signal indicative of the rate of the ice accretion can be based on a slope of the measured frequency of resonance with respect to time. The ice-phase detection system can generate a signal indicative of the liquid-water content of the cloud. The generated signal is indicative of the liquid-water content can be based on the slope of the measured frequency of resonance with respect to time.

A further embodiment of any of the foregoing cloud phase detectors, wherein the liquid-water detection system can calculate, based on the received signals of the airspeed and the angle of attack as well as the signal indicative of the temperature of the cloud, one or more critical temperatures corresponding to one or more surface locations on the aircraft, respectively. The one or more critical temperatures can be indicative of a temperature below which a portion of the liquid-water content can freeze on the respective surface location.

A further embodiment of any of the foregoing cloud phase detectors, wherein the liquid-water detection system can calculate, based on the received signals of the airspeed and the angle of attack as well as the signal indicative of the temperature of the cloud, one or more Ludlam temperatures corresponding to one or more surface locations on the aircraft, respectively. The one or more Ludlam temperatures indicative of a temperature below which all of the liquid-water content can freeze on the respective surface location.

A further embodiment of any of the foregoing cloud phase detectors, wherein the liquid-water detection system can be configured to generate a signal indicative of the liquid-water content if one of the detected resonant frequency is less than the baseline resonant frequency and the detected temporal variations of the resonant frequency are greater than a predetermined threshold.

A further embodiment of any of the foregoing cloud phase detectors, wherein the liquid-water detection system can be configured to generate a signal indicative of the liquid-water content if both the detected resonant frequency is the first threshold less than the baseline resonant frequency and the detected temporal variations of the resonant frequency are greater than the second threshold.

A liquid-water content calculator includes a magnetostrictive resonator having a baseline resonant frequency in an ice-free and liquid-water-free condition. The magnetostrictive resonator is configured to resonate at a resonant frequency indicative of a measure of ice accretion on an exterior surface of the magnetostrictive resonator. The liquid-water content calculator includes a frequency detector configured to detect the resonant frequency of the magnetostrictive resonator. The liquid-water content calculator includes a noise detector configured to detect temporal variations of the resonant frequency of the magnetostrictive resonator. The liquid-water content calculator includes a liquid-water detection system configured to generate a signal indicative of the liquid-water content if either the detected resonant frequency is a first threshold less than the baseline resonant frequency or the detected temporal variations of the resonant frequency are greater than a second threshold. The liquid-water content calculator includes an ambient temperature detector configured to generate a signal indicative of an ambient temperature. The liquid-water content calculator includes an airspeed indicator configured to detect airspeed of an aircraft. The liquid-water content calculator includes an angle-of-attack sensor configured to detect an angle of attack of the aircraft. The liquid-water content calculator also includes a critical temperature calculator configured to calculate, based on the detected airspeed, the detected angle of attack, the detected ambient temperature, the detected resonant frequency, and the detected temporal variations of the resonant frequency, one or more critical temperatures corresponding to one or more locations on an aircraft surface, respectively. The one or more critical temperatures are indicative of a temperature below which a freezing fraction of the liquid-water content is greater than zero.

A further embodiment of the foregoing liquid-water content calculator, wherein the liquid-water detection system can calculate, based on the received signals of the airspeed and the angle of attack as well as the signal indicative of the temperature of the cloud, one or more Ludlam temperatures corresponding to one or more surface locations on the aircraft, respectively. The one or more Ludlam temperatures indicative of a temperature below which all of the liquid-water content can freeze on the respective surface location.

A further embodiment of any of the foregoing liquid-water content calculators, wherein the liquid-water detection system can be configured to generate a signal indicative of liquid-water content if both of the detected resonant frequency is the first threshold less than the baseline resonant frequency and the detected temporal variations of the resonant frequency are greater than the second threshold.

A further embodiment of any of the foregoing liquid-water content calculators, wherein the liquid-water detection system can generate a signal indicative of a rate of the ice accretion, the signal indicative of a rate of the ice accretion based on a slope of the measured frequency of resonance with respect to time exceeds a predetermined threshold.

A further embodiment of any of the foregoing liquid-water content calculator, wherein the liquid-water detection system can generate a signal indicative of water content if the slope of the measured frequency of resonance is less than the predetermined threshold.

A method for determining liquid-water content in a cloud includes presenting a resonator in a cloud. The method includes magnetostrictively resonating the resonator. The method includes determining a baseline resonant frequency of the resonator. The method includes measuring a frequency of resonance of the resonator in the cloud. The method includes comparing the measured frequency of resonance with the determined baseline resonant frequency. The method includes determining a temporal variation of the measured frequency of resonance. The method includes comparing the determined temporal variation of the measured frequency of resonance with a predetermined threshold. The method includes generating a signal indicative of liquid-water content. The generated signal indicative of liquid-water content is zero if the compared frequency of resonance is not less than the determined baseline resonant frequency and the compared temporal variation is not greater than the predetermined threshold. The generated signal indicative liquid-water content is greater than zero if either the compared frequency of resonance is a first threshold less than the determined baseline resonant frequency or the compared temporal variation is greater than a second threshold.

The method of the preceding paragraph can optionally include, additionally and/or alternatively, any one or more of the following features, configurations and/or additional components: generating a signal indicative of the ambient temperature; detecting airspeed of an aircraft; detecting angle of attack of the aircraft; calculating, based on the detected airspeed, the detected angle of attack, the detected ambient temperature, the detected resonant frequency, and/or the detected temporal variations of the resonant frequency, one or more critical temperatures corresponding to one or more locations on an aircraft surface, respectively. The one or more critical temperatures indicative of a temperature below which a freezing fraction of the water content is greater than zero.

A further embodiment of any of the foregoing methods, wherein first threshold can be at least three ten thousandths of the baseline frequency less than the baseline resonant frequency.

A further embodiment of any of the foregoing methods, wherein the second threshold can be at least three ten thousandths of the baseline resonant frequency.

A further embodiment of any of the foregoing methods, wherein the generated signal indicative liquid-water content is greater than zero if both the compared frequency of resonance is the first threshold less than the determined baseline resonant frequency and the compared temporal variation is not greater than the second threshold.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A cloud phase detector comprising:
a magnetostrictive resonator having a baseline resonant frequency in an ice-free and liquid-water-free condition, the magnetostrictive resonator configured to resonate at a resonant frequency indicative of a measure of ice accretion upon an exterior surface of the magnetostrictive resonator;
a processor; and
computer-readable memory encoded with instructions that, when executed by the processor, cause the cloud phase detector to:
detect the resonant frequency of the magnetostrictive resonator;
detect temporal variations of the resonant frequency of the magnetostrictive resonator; and
generate a signal indicative of liquid-water content if either the detected resonant frequency is a first threshold less than the baseline resonant frequency or the detected temporal variations of the resonant frequency are greater than a second threshold.

2. The cloud phase detector of claim 1, further comprising:
a temperature sensor configured to generate a signal indicative of a temperature of an exterior surface of the cloud phase detector.

3. The cloud phase detector of claim 2, further comprising:
a digital communications interface configured to receive digital communications from an aircraft instrumentation bus, the received digital communications including a signal indicative of airspeed of an aircraft and a signal indicative of an angle of attack of the aircraft,
wherein the computer-readable memory is further encoded with instructions that, when executed by the processor, cause the cloud phase detector to:
calculate, based on the received signals of the airspeed and the angle of attack as well as the signal indicative of the temperature, one or more critical temperatures corresponding to one or more surface locations on the aircraft, respectively, the one or more critical temperatures indicative of a temperature below which a portion of the liquid-water content can freeze on the one or more corresponding surface locations.

4. The cloud phase detector of claim 3, wherein the computer-readable memory is further encoded with instructions that, when executed by the processor, cause the cloud phase detector to:
calculate, based on the received signals of the airspeed and the angle of attack as well as the signal indicative of the temperature, one or more Ludlam temperatures corresponding to one or more surface locations on the aircraft, respectively, the one or more Ludlam temperatures indicative of a temperature below which all of the liquid-water content can freeze on the one or more respective surface locations.

5. The cloud phase detector of claim 1, wherein the computer-readable memory is further encoded with instructions that, when executed by the processor, cause the cloud phase detector to:
generate a signal indicative of the liquid-water content if both the detected resonant frequency is the first threshold less than the baseline resonant frequency and the detected temporal variations of the resonant frequency are greater than the second threshold.

6. The cloud phase detector of claim 1, wherein the computer-readable memory is further encoded with instructions that, when executed by the processor, cause the cloud phase detector to:
generate a signal indicative of a rate of the ice accretion, the signal indicative of the rate of the ice accretion based on a slope of the detected resonant frequency with respect to time.

7. The cloud phase detector of claim 6, wherein the computer-readable memory is further encoded with instructions that, when executed by the processor, cause the cloud phase detector to:
generate a signal indicative of the liquid-water content, the generated signal indicative of the liquid-water content based on the slope of the detected resonant frequency with respect to time.

8. The cloud phase detector of claim 1, wherein the computer-readable memory is further encoded with instructions that, when executed by the processor, cause the cloud phase detector to:
generate a signal indicative of the liquid-water content if either the detected resonant frequency is at least three ten thousandths the baseline resonant frequency less than the baseline resonant frequency and the detected temporal variations of the resonant frequency are greater than two ten thousandths of the baseline resonant frequency.

9. A liquid-water content calculator comprising:
a magnetostrictive resonator having a baseline resonant frequency in an ice-free and liquid-water-free condition, the magnetostrictive resonator configured to resonate at a resonant frequency indicative of a measure of ice accretion on an exterior surface of the magnetostrictive resonator;
an airspeed indicator configured to detect airspeed of an aircraft;
an angle-of-attack sensor configured to detect an angle of attack of the aircraft;
a processor; and
computer-readable memory encoded with instructions that, when executed by the processor, cause the liquid-water content calculator to:
detect the resonant frequency of the magnetostrictive resonator;
detect an ambient temperature;
detect temporal variations of the resonant frequency of the magnetostrictive resonator; and
generate a signal indicative of liquid-water content if either the detected resonant frequency is a first threshold less than the baseline resonant frequency or the detected temporal variations of the resonant frequency are greater than a second threshold; and
calculate, based on the detected airspeed, the detected angle of attack, the detected ambient temperature, the detected resonant frequency, and the detected temporal variations of the resonant frequency, one or more critical temperatures corresponding to one or more locations on an aircraft surface, respectively, the one or more critical temperatures indicative of a temperature below which a freezing fraction of the liquid-water content is greater than zero.

10. The liquid-water content calculator of claim 9, wherein the computer-readable memory is further encoded with instructions that, when executed by the processor, cause the liquid-water content calculator to:
calculate, based on the received signals of the airspeed and the angle of attack as well as the signal indicative of the temperature, one or more Ludlam temperatures corresponding to one or more surface locations on the aircraft, respectively, the one or more Ludlam temperatures indicative of a temperature below which all of the liquid-water content can freeze on the one or more corresponding surface locations.

11. The liquid-water content calculator of claim 10, wherein the computer-readable memory is further encoded with instructions that, when executed by the processor, cause the liquid-water content calculator to:
generate a signal indicative of liquid-water content if both of the detected resonant frequency is less than the baseline resonant frequency and the detected temporal variations of the resonant frequency are greater than one ten thousandth of the baseline resonant frequency.

12. The liquid-water content calculator of claim 9, wherein the computer-readable memory is further encoded with instructions that, when executed by the processor, cause the liquid-water content calculator to:
generate a signal indicative of a rate of the ice accretion, the signal indicative of the rate of the ice accretion based on a slope of the detected resonant frequency with respect to time.

13. The liquid-water content calculator of claim 12, wherein the computer-readable memory is further encoded with instructions that, when executed by the processor, cause the liquid-water content calculator to:
generate a signal indicative of water content if the slope of the detected resonant frequency is less than the predetermined threshold.

14. A method for determining liquid-water content in a cloud, the method including:
presenting a resonator in a cloud;
magnetostrictively resonating the resonator;
determining a baseline resonant frequency of the resonator;
measuring a frequency of resonance of the resonator in the cloud;
comparing the measured frequency of resonance with the determined baseline resonant frequency;
determining a temporal variation of the measured frequency of resonance;
comparing the determined temporal variation of the measured frequency of resonance with a predetermined threshold;
generating a signal indicative of liquid-water content, wherein the generated signal indicative of liquid-water content is zero if the compared frequency of resonance is not less than the determined baseline resonant frequency and the compared temporal variation is not greater than the predetermined threshold, and wherein the generated signal indicative liquid-water content is greater than zero if either the compared frequency of resonance is a first threshold less than the determined baseline resonant frequency or the compared temporal variation is greater than predetermined second threshold.

15. The method of claim 14, wherein the first threshold is at least three ten thousandths of the baseline frequency less than the baseline resonant frequency.

16. The method of claim 14, wherein the second threshold is at least to three ten thousandths of the baseline resonant frequency.

17. The method of claim 14, wherein the generated signal indicative liquid-water content is greater than zero if both the compared frequency of resonance is the first threshold less than the determined baseline resonant frequency and the compared temporal variation is not greater than the second threshold.

18. The method of claim 14, further comprising:
generating a signal indicative of the ambient temperature.

19. The method of claim 18, further comprising:
detecting airspeed of an aircraft; and
detecting angle of attack of the aircraft.

20. The method of claim 19 further comprising:
calculating, based on the detected airspeed, the detected angle of attack, the detected ambient temperature, the detected resonant frequency, and the detected temporal variations of the resonant frequency, one or more critical temperatures corresponding to one or more locations on an aircraft surface, respectively, the one or more critical temperatures indicative of a temperature below which a freezing fraction of the water content is greater than zero.

* * * * *